US012497280B1

(12) United States Patent
Ward et al.

(10) Patent No.: US 12,497,280 B1
(45) Date of Patent: Dec. 16, 2025

(54) CLEAN IN PLACE SYSTEM FOR A BEVERAGE DISPENSER

(71) Applicants: Peter Ward, Tulsa, OK (US); David James Keener, Tulsa, OK (US)

(72) Inventors: Peter Ward, Tulsa, OK (US); David James Keener, Tulsa, OK (US)

( * ) Notice: Subject to any disclaimer, the term of this patent is extended or adjusted under 35 U.S.C. 154(b) by 404 days.

(21) Appl. No.: 18/081,866

(22) Filed: Dec. 15, 2022

Related U.S. Application Data

(60) Provisional application No. 63/290,490, filed on Dec. 16, 2021.

(51) Int. Cl.
*B67D 1/07* (2006.01)
*A61L 2/18* (2006.01)
*A61L 2/26* (2006.01)
*B08B 9/032* (2006.01)

(52) U.S. Cl.
CPC .................. *B67D 1/07* (2013.01); *A61L 2/18* (2013.01); *A61L 2/26* (2013.01); *B08B 9/0325* (2013.01); *A61L 2202/15* (2013.01); *A61L 2202/17* (2013.01); *B08B 2209/032* (2013.01); *B67D 2001/075* (2013.01)

(58) Field of Classification Search
None
See application file for complete search history.

(56) References Cited

U.S. PATENT DOCUMENTS 9,797,652 B1 * 10/2017 Wilkerson ............ F25D 31/002
2021/0347624 A1 * 11/2021 Newton ............... B67D 1/0051

* cited by examiner

*Primary Examiner* — Eric W Golightly
(74) *Attorney, Agent, or Firm* — Head, Johnson, Kachigian & Wilkinson, PC

(57) ABSTRACT

A system and method to automatically clean the lines of a beverage dispenser system by purging the beverage lines, then de-liming, purging again, sanitizing, rinsing and recharging the lines. The present invention has a series of reservoirs, pumps and solenoid operated valves all run by an automated controller which carries out the cleaning process without human intervention.

4 Claims, 2 Drawing Sheets

CLEAN IN PLACE SYSTEM FOR A BEVERAGE DISPENSER

CLAIM OF PRIORITY

The present application claims the priority to U.S. Provisional Patent Application No. 63/290,490, filed on Dec. 16, 2021, entitled a Clean in Place System For A Beverage Dispenser, which is incorporated herein by reference.

FIELD OF THE INVENTION

The present invention relates generally to a beverage dispenser system. More particularly, the present invention relates to a clean in place system for a beverage dispenser.

BACKGROUND OF THE INVENTION

Consumers are becoming more accustomed to an increasing array of premium flavored beverages. These beverages range from hot and cold coffees infused with nitrogen and cream-based flavoring to flavored teas and a wide range of premium beers. Regardless of the type of beverage, the dispenser must be maintained. One of the most neglected parts of this maintenance is cleaning the supply lines. These are the conduits which carry the beverage from their storage reservoir to the dispensing head. They often run from a refrigerated storage reservoir through an ambient temperature area to the dispensing head.

Ideally these lines should be cleaned every few days. The exact interval between cleaning depends on a number of factors such as the type of beverage, sugar content, dairy content, hardness of the water used, temperature of the beverage and ambient temperature. If cleaning maintenance is delayed or ignored the taste and texture of these beverages can be negatively impacted. In extreme cases it can become a health issue and/or prevent the efficient operation of the dispenser.

Manual cleaning of these lines requires a significant amount of labor to carry out the various steps. In a complete cleaning the line is purged with water. The line is then charged with a de-limer solution which is allowed to sit in the line to loosen and remove lime deposits. Next the line is rinsed with water to remove the loosened debris. The line is then charged with a sanitizing solution which is allowed to sit in the line to kill any germs and bacteria. The sanitizer is then rinsed from the line with water. Finally, the line is recharged with beverage prior to being put back in service.

As can be imagined it takes a significant amount of time and effort to ensure these steps are carried out and the lines are properly cleaned. Most dispensers typically have several lines so that labor is further increased. What is needed, therefore, is a system that can automatically clean and sanitize these beverage dispensers without constant human intervention.

BRIEF SUMMARY OF THE INVENTION

The present invention achieves its objections by providing a system and method to automatically clean these lines by purging the beverage lines, then delime, purge again, sanitize, rinse and recharge the lines. The present invention has a series of reservoirs, pumps and solenoid operated valves all run by an automated controller which carries out the cleaning process without human intervention.

While the present invention can be used on any number of beverage dispensing systems, it is explained here on a system that dispenses a nitrogen infused beverage. Likewise, it can be used on hot or cold beverages dispenser. Often the difference between a hot or cold dispenser is the presence of a flash heater near the dispensing head. The flash heater raises the temperature of the beverage to an acceptable temperature for a "steaming" cup of coffee, cocoa or tea just prior to it being dispensed into a cup or other serving container.

BRIEF DESCRIPTION OF THE DRAWINGS

Preferred embodiments of the invention will now be described in further detail. Other features, aspects, and advantages of the present invention will become better understood with regard to the following detailed description, appended claims, and accompanying drawings (which are not to scale) where:

DETAILED DESCRIPTION OF THE PREFERRED EMBODIMENT(S)

The present invention is a system and method for automatically cleaning the supply lines on a beverage dispenser 20. Such dispensers 20 could have a single dispensing head or multiple dispensing heads 22. Similarly, it could be used to dispense hot or cold beverages. These could be uncarbonated, carbonated or infused with other gases such as nitrogen. In short, the present invention should not be viewed to be limited to a specific type of beverage or beverage dispenser system 20. For illustration purposes the present invention is described on a beverage dispenser system 20 with nitrogen infusion.

Figure 1:
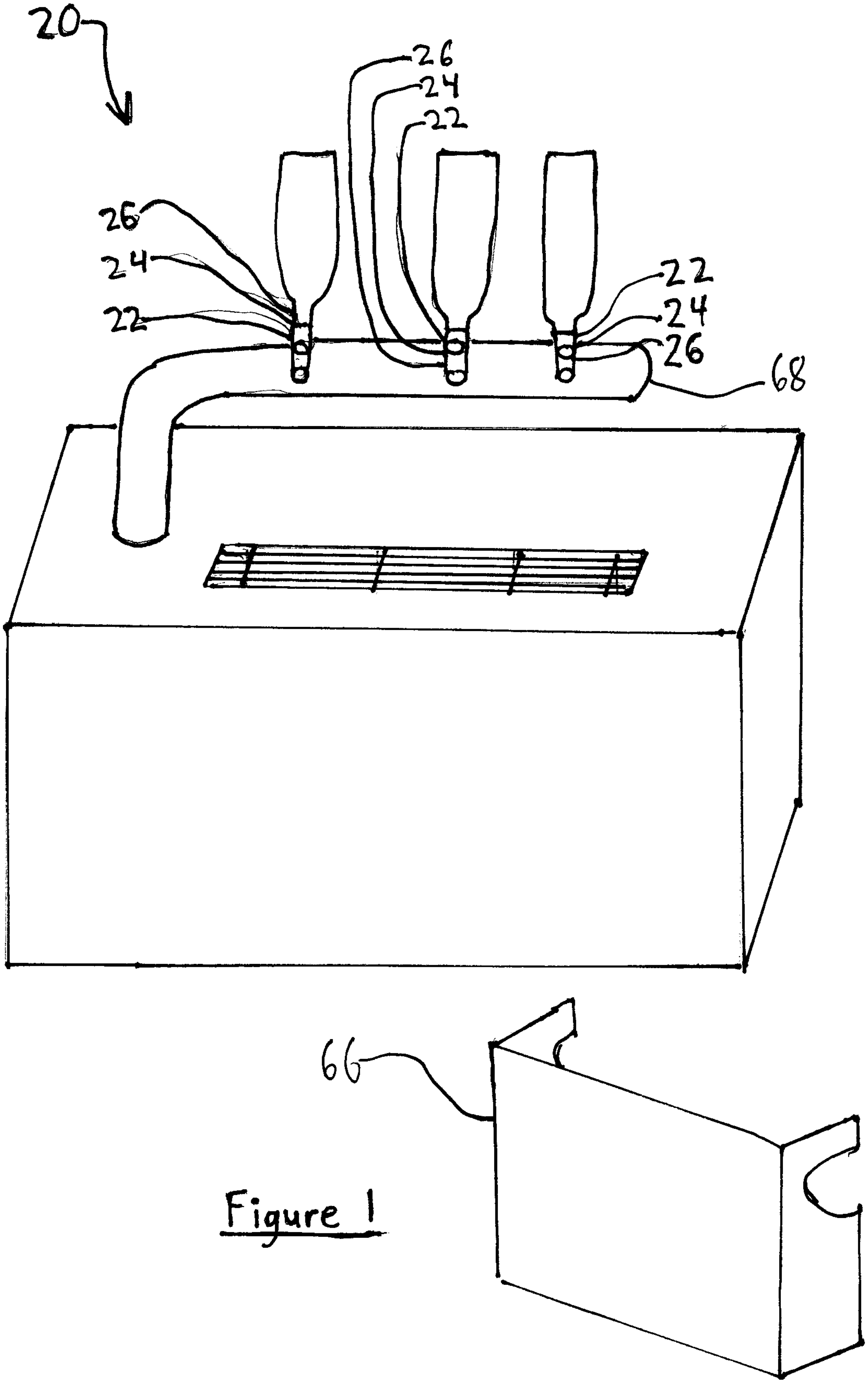
FIG. 1 is a perspective view of a beverage dispenser system with the preferred embodiment of the present invention.
Figure 2:
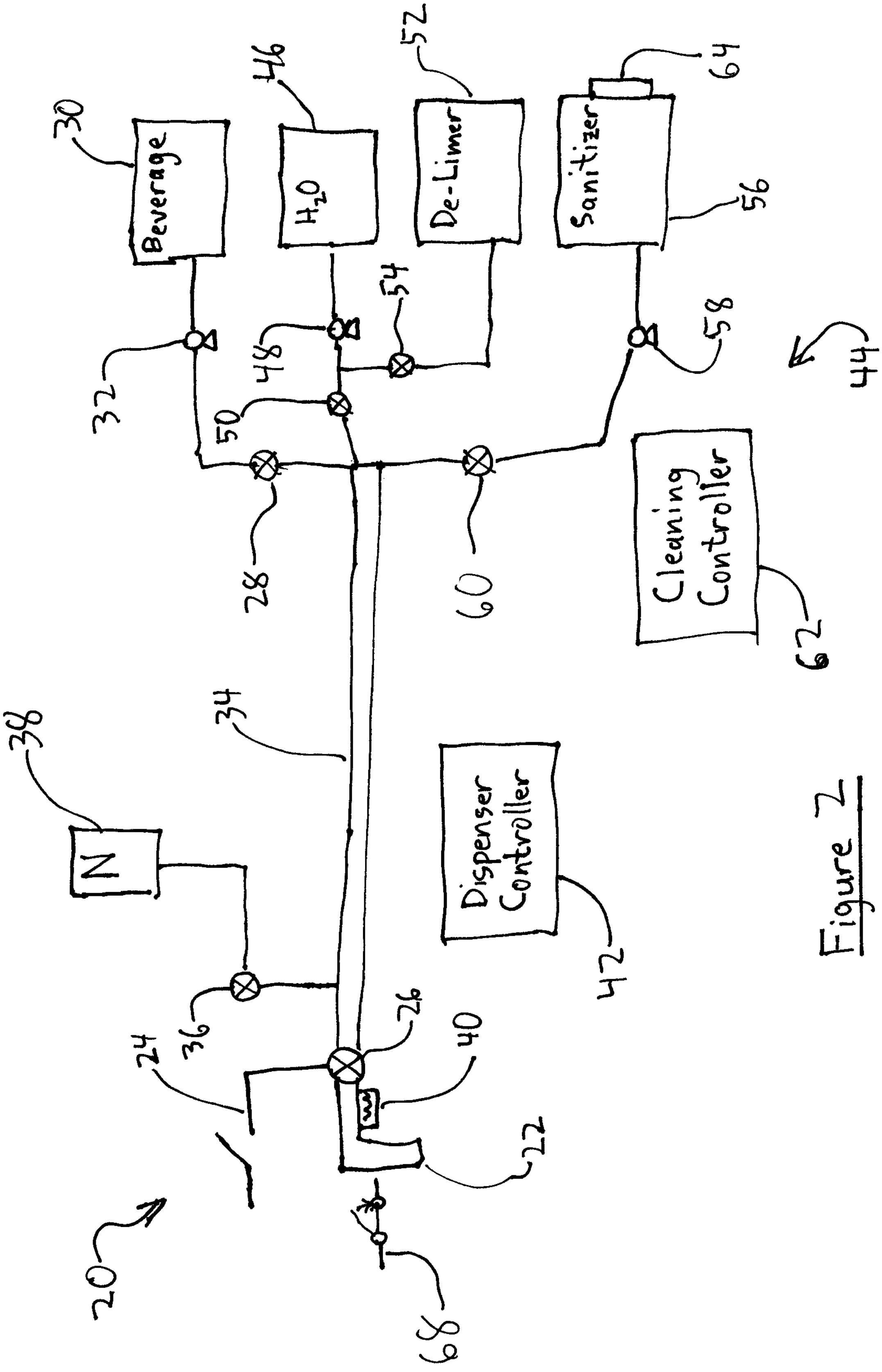
FIG. 2 is a schematic of one dispensing head and its related equipment.

Turning now to the drawings wherein like reference characters indicate like or similar parts throughout, FIG. 1 is a perspective view of a dispenser system 20 with the preferred embodiment of the present invention. The dispenser system 20 has one or more dispensing heads 22. FIG. 2 provides a schematic of the preferred embodiment of the present invention installed on a single beverage dispensing head 22. The present invention can be tied to multiple dispensing heads 22 on beverage dispenser system 20.

In the preferred embodiment the dispenser system 20 has a plurality of dispensing heads 22. Each head 22 has a head switch 24, a solenoid operated head valve 26, a solenoid operated beverage valve 28, a beverage reservoir 30, a beverage pump 32, a dispensing conduit 32 and a nitrogen injector 36. The head switch 24 is configured such that when it is depressed the head valve 26 and the solenoid operated beverage valve 26 open and the beverage pump 32 begins to operate. This places the beverage reservoir 30 in fluid communication with the dispensing conduit 34 and allows the beverage to flow from the beverage reservoir 30 and out the dispensing head 22.

If equipped for a nitrogen infused beverage, the nitrogen injector 36 is opened after a predetermined timed delay (typically less than one second). This puts the dispensing conduit 34 in fluid communication with a nitrogen supply 38 and allows nitrogen to be injected into the beverage flowing through the dispensing conduit 34.

If the dispensing head 22 is for dispensing a hot beverage it will also be equipped with a flash heater 40. In use, this can be energized when the head valve 26 is opened or delayed to energized when the nitrogen injector 36 is opened.

In the preferred embodiment, operation of the dispenser system 20 is controlled by dispenser controller 42 which is configured to receive a start signal from the head switches 24 and run the operation of the various pumps 32, solenoid operated valves 26, 28, injectors 36 and heater 40. The predetermined length of time of delays for operation of the various components is programmed into the dispenser controller 42.

The present invention improves to the beverage dispensing system 20 by adding a clean in place system 44 which automatically rinses, delimes, sanitizes and recharges the dispensing conduit 34. In the preferred embodiment the clean in place system 44 has water supply 46, water pump 48, solenoid operated water valve 50, a de-limer reservoir 52 and a solenoid operated de-limer valve 54, a sanitizer reservoir 56, a sanitizer pump 58, a sanitizer operated sanitizer valve 60 and a cleaning controller 62.

In the preferred embodiment once the cleaning controller 62 is activated the head switches 24 and dispensing controller 42 on the dispenser system 20 are disabled or otherwise locked out of operation. A level sensor 64 on the sanitizer reservoir 56 is used to confirm it is full. The cleaning controller 62 then confirms the nitrogen injector 36 is closed and if not, closes it. The dispensing conduits 34 are then purged by flushing them with water for a predetermined length of time. The conduits 34 may be flushed individually or all of them simultaneously. This is accomplished by opening the head valve 26 on the conduits 34 to be flushed and opening the corresponding solenoid operated water valve 50 and operating the water pump 48.

Once the dispenser conduits 34 are purged they are delimed. This is accomplished by opening the solenoid operate de-limer valve 54 while the head valve 26 and solenoid operated water valve 50 are open and the water pump 48 is operating for a predetermined length of time. A venturi action pulls de-limer from the de-limer reservoir 52 and into the water as it is pumped into the dispensing conduit 34. Once the dispensing conduits 34 are charged with de-limer, the water pump 48 is stopped and the head valve 26, solenoid operated water valve 50 and solenoid operated de-limer valve 54 are closed and the de-limer is allowed to sit in the dispensing conduit 34 for a predetermined length of time, preferably 5 to 15 minutes.

The dispensing conduits 34 are then purged of the de-limer with water. This is accomplished by opening the head valve 26 on the conduits 34 to be flushed and opening the corresponding solenoid operated water valve 50 and operating the water pump 48 for a predetermined length of time.

The dispensing conduits 34 are then sanitized. This is accomplished by opening the head valve 26 on the conduits 34 and opening the corresponding solenoid operated sanitizer valve 60 and operating the sanitizer pump 58 for a predetermined length of time. Once the dispensing conduits 34 are charged with sanitizer the sanitizer pump 58 is stopped and the head valve 26 and solenoid operated sanitizer valve 60 are closed and the sanitizer is allowed to sit in the dispensing conduit 34 for a predetermined length of time, preferably 5 to 15 minutes.

The sanitizer in the dispensing conduits 34 is then purged with water. This is accomplished by opening the head valve 26 on the conduits 34 to be flushed and opening the corresponding solenoid operated water valve 50 and operating the water pump 48 for a predetermined length of time.

The dispensing conduit 34 is then recharged with beverage. This is done by opening the head valve 26 on the conduits and the corresponding solenoid operated beverage valve 28 and operating the beverage pump 32 for a predetermined length of time. This length of time may vary but should be sufficiently long enough to purge the water remaining in the dispensing conduit 34.

Control and operation of the various solenoid operated valves, pumps and reading of the level sensors during the cleaning process is done by the cleaning controller 62. In the preferred embodiment cleaning controller is placed in communication with each of these components using RS485 communications cabling and related protocols. However, this could be carried out by other means and still be withing the scope of the present invention.

In the preferred embodiment the various solenoid operated valves remain closed until operated or opened. This means they only remain open as long as they are receiving power. If they remain open an extended length of time, such as when rinsing the conduit 34, the constant supply of power can over heat the solenoid and cause a malfunction or failure of the solenoid. In the preferred embodiment the controllers 42 and 62 send power to the solenoids in a pulse width modulated format this reduces the total amount of power sent to the solenoid and avoids heat buildup.

The cleaning system 44 can be set to run various programs or cleaning routines which can vary the length of time the de-limer and sanitizer are pumped into and/or held in the dispensing conduit 34 as well as the predetermined length of time water is allowed flow through the dispensing conduit 34 while rinsing or purging. Thus, the cleaning controller 62 may have several cleaning programs or modes providing a range of cleaning options such as a quick clean cycle or a longer more thorough deep clean cycle.

The cleaning system 44 may also include a shield 66 which can be secured to the front of the dispenser system 20 blocking access to the dispensing heads 22. This prevents employees and customers from interrupting the cleaning system 44 while it is running a cleaning cycle. Further this dispenser system 20 may be equipped with an isolation switch 68 that is triggered when the shield 66 is put in place. In the preferred embodiment the isolation switch 68 deactives the dispenser controller 42 when the shield 66 is put in place this further prevents operation of the head switches 24 on the dispenser system 20 and interference with the cleaning system 44 during a cleaning cycle.

In one embodiment the isolation switch 68 is a magnetically operated reed switch and the shield is a ferrous metal. The isolation switch 68 is located on the dispenser system 20 such that when the shield 66 is put in place the shield 66 the switch 68 is triggered by a portion of the shield 66.

The foregoing description details certain preferred embodiments of the present invention and describes the best mode contemplated. It will be appreciated, however, that changes may be made in the details of construction and the configuration of components without departing from the spirit and scope of the disclosure. Therefore, the description provided herein is to be considered exemplary, rather than limiting, and the true scope of the invention is that defined by the following claims and the full range of equivalency to which each element thereof is entitled.

What is claimed is:

1. A line cleaning system for a beverage dispenser, said line cleaning system comprising:

a beverage dispenser system with a plurality of dispensing heads each head having a beverage reservoir, a dispensing conduit, a head valve, a solenoid operated beverage valve, a beverage pump and a head switch, the head switch configured to operate the head valve, the solenoid operated beverage valve, and the beverage pump, wherein upon activations of the head switch the dispensing conduit is placed in fluid communication with the head switch, the solenoid operated beverage valve, the beverage reservoir and the beverage pump;

a de-limer reservoir, and solenoid operated de-limer valve, all in fluid communication with each dispensing head, the solenoid operated de-limer valve configured to selectively isolate the de limer reservoir from the dispensing conduit;

a sanitizer reservoir, sanitizer pump and solenoid operated sanitizer valve, all in fluid communication with each dispensing head and the solenoid operated sanitizer valve configured to selectively isolate the sanitizer reservoir and pump from the dispensing heads;

a nitrogen reservoir;

a plurality of nitrogen injectors, each nitrogen injector in fluid communication with the nitrogen reservoir, each dispensing head in fluid communication with one of the nitrogen injectors, the nitrogen injectors being configured to selectively isolate their respective dispensing head from the nitrogen reservoir; and a dispenser controller;

wherein when one of the head switches is activated the dispenser controller opens the head valve of the respective dispenser head and activates the respective beverage pump, putting the dispenser head in fluid communication with the respective beverage reservoir, and following a timed delay the controller opens the nitrogen injector of the respective dispensing head, placing the nitrogen reservoir in fluid communication with the respective dispensing head.

2. The system of claim 1, further comprising:

wherein when the respective head switch is deactivated, the dispenser controller closes the dispensing solenoid operated valve, beverage solenoid operated valve and nitrogen injector of the respective dispensing head and stops the beverage pump of the respective dispensing head.

3. The system of claim 1 further comprising:

a water supply with a solenoid operated valve configured to selectively place the water supply in fluid communication with the dispensing conduits, a water supply pump, a cleaner controller, wherein the cleaner controller is configured to, upon activation, lock out the dispenser controller from operation, confirm the sanitizer reservoir is full, close the nitrogen injectors, open the dispensing solenoid operated valve, open the water supply solenoid operated valve to flush the dispensing conduits for a predetermined length of time, then open the de-limer solenoid operated valve to allow de-limer infused water to fill the dispensing conduit for a predetermined length of time, then close the dispensing solenoid operated valve, water supply solenoid operated valve and the de-limer solenoid operated, then after a predetermined length of time open the dispensing solenoid operated valve and the water supply solenoid operated valve and operate the water supply pump for a predetermined time, then close the water supply solenoid operated valve and open the sanitizer solenoid operated valve and operate the sanitizer pump for a predetermined length of time, then close the dispensing solenoid operated valve and the sanitizer solenoid operated valve, then after a predetermined length of time open the dispensing solenoid operated valve and the water supply operated valve and operate the water supply pump for a predetermined length of time, then close the water supply solenoid operated valve and open the beverage solenoid operated valve and operate the beverage pump for a predetermined length of time, then close the dispensing solenoid operated valve and the beverage solenoid operated valve.

4. The system of claim 1 further comprising:

a magnetic operated switch located on one of the plurality of dispensing heads, and a shield, wherein when the shield is mounted adjacent to one of the dispensing heads, it blocks access to the adjacent dispensing head and triggers the magnetic operated switch which disengages the dispenser controller.

* * * * *